United States Patent
Cramer et al.

[11] Patent Number: 6,096,067
[45] Date of Patent: *Aug. 1, 2000

[54] DISPOSABLE THERMAL BODY PAD

[75] Inventors: Ronald Dean Cramer, Cincinnati; Leane Kristine Davis, Milford; William Robert Ouellette, Cincinnati, all of Ohio

[73] Assignee: The Procter & Gamble Company, Cincinnati, Ohio

[*] Notice: This patent is subject to a terminal disclaimer.

[21] Appl. No.: 08/777,856

[22] Filed: Dec. 31, 1996

[51] Int. Cl.[7] ........................................... A61F 7/00
[52] U.S. Cl. ........................ 607/96; 607/108; 607/112
[58] Field of Search ..................... 607/96, 104, 108–112, 607/114; 165/46; 126/204; 602/2; 62/4; 264/53

[56]         References Cited

U.S. PATENT DOCUMENTS

| Re. 32,026 | 11/1985 | Yamashita et al. | 126/263 |
|---|---|---|---|
| 3,900,035 | 8/1975 | Welch et al. | 128/402 |
| 3,939,237 | 2/1976 | Naito et al. | |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,516,564 | 5/1985 | Koiso et al. | 126/263 |
| 4,522,190 | 6/1985 | Kuhn et al. | 126/263 |
| 4,573,447 | 3/1986 | Thrash et al. | 607/111 X |
| 4,575,097 | 3/1986 | Brannigan et al. | 128/402 |
| 4,649,895 | 3/1987 | Yasuki et al. | 126/263 |

(List continued on next page.)

FOREIGN PATENT DOCUMENTS

| 0 370 600 A1 | 7/1989 | European Pat. Off. | F24J 1/00 |
|---|---|---|---|
| 160443 | 9/1983 | India | C09K 3/02 |
| 56-145846 | 11/1981 | Japan | A61F 7/03 |
| 57-170252 | 10/1982 | Japan | A61F 7/03 |
| 58-37075 | 3/1983 | Japan | C09K 5/00 |
| 3-100090 | 4/1991 | Japan | C09K 5/00 |
| 5-317188 | 12/1993 | Japan | A47J 36/28 |
| 6-1969 | 1/1994 | Japan | C09K 5/00 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-112006 | 5/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-80317 | 3/1996 | Japan | A61F 7/08 |
| 8-98856 | 4/1996 | Japan | A61F 7/08 |
| 8-126656 | 5/1996 | Japan | A61F 7/08 |
| 2 205 496 | 12/1988 | United Kingdom | A61F 7/03 |
| 2 297 490 | 8/1996 | United Kingdom | A61F 7/03 |
| WO 94/00087 | 1/1994 | WIPO | A61F 7/00 |

*Primary Examiner*—Jeffrey J. Jastrzab
*Assistant Examiner*—Ryan Carter
*Attorney, Agent, or Firm*—Loy M. White; Douglas C. Mohl; T. David Reed

[57]           ABSTRACT

The present invention relates to disposable thermal body pads comprising one or more thermal packs having a unified structure of at least one continuous layer of a semirigid material which softens when heated and a plurality of individual heat cells, which typically comprise an exothermic composition, spaced apart and fixedly attached across the thermal pack. The material of the continuous layer or layers provide sufficient rigidity to maintain structural support of the heat cells, to prevent unacceptable stretching of structures of the continuous layer or layers during processing or use of the thermal pads, and to ensure child resistance, while also providing good overall drape characteristics when heated. The disposable thermal body pads are intended to be attached to a user's clothing on one side and to be held directly against the user's skin on the other side, for pain relief. More particularly, the present invention relates to disposable thermal body pads having good conformity to user's body which provides consistent, convenient and comfortable heat application. Even more particularly, the present invention relates to such disposable thermal body pads intended for relieving menstrual pain.

21 Claims, 2 Drawing Sheets

U.S. PATENT DOCUMENTS

| | | | |
|---|---|---|---|
| 4,671,267 | 6/1987 | Stout | 607/114 X |
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 4,995,126 | 2/1991 | Matsuda | 5/421 |
| 5,046,479 | 9/1991 | Usui | 126/204 |
| 5,062,269 | 11/1991 | Siegel | 62/4 |
| 5,179,944 | 1/1993 | McSymytz | 128/403 |
| 5,190,033 | 3/1993 | Johnson | 128/403 |
| 5,233,981 | 8/1993 | Miyashita | 607/114 |
| 5,342,412 | 8/1994 | Ueki | 607/114 |
| 5,366,491 | 11/1994 | Ingram et al. | 607/108 |
| 5,366,492 | 11/1994 | Ueki | 607/114 |
| 5,674,270 | 10/1997 | Viltro et al. | 607/112 |

DISPOSABLE THERMAL BODY PAD

TECHNICAL FIELD

The present invention relates to disposable thermal body pads comprising one or more thermal packs having a unified structure of at least one continuous layer of a semirigid material which softens when heated and a plurality of individual heat cells, which typically comprise an exothermic composition, spaced apart and fixedly attached across the thermal pack. The material of the continuous layer or layers provide sufficient rigidity to maintain structural support of the heat cells, to prevent unacceptable stretching of structures of the continuous layer or layers during processing or use of the thermal pads, and to ensure child resistance, while also providing good overall drape characteristics when heated. The disposable thermal body pads are intended to be attached to a user's clothing on one side and to be held directly against the user's skin on the other side, for pain relief. More particularly, the present invention relates to disposable thermal body pads having good conformity to user's body which provides consistent, convenient and comfortable heat application. Even more particularly, the present invention relates to such disposable thermal body pads intended for relieving menstural pain.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like. These treatments include the use of whirlpools, hot towels, hydrocollators, heating pads and elastic compression bands. Many of these devices employ reusable thermal packs containing, e.g., water and microwaveable gels. In general, such devices which require the thermal source to be replenished are inconvenient to use. Further, many of these thermal units or devices do not provide long lasting heat and also do not maintain a consistent temperature over long periods of time. Depending on the length of exposure, the skin temperature needs to be maintained from about 35° C. to about 55° C., preferably from about 36° C. to about 45° C., more preferably from about 37° C. to about 43° C., and most preferably from about 38° C. to about 42° C., to achieve the desired therapeutic benefits.

The beneficial therapeutic effects from this administration of heat diminish after the heat source is removed. Therefore, depending on the temperature, it is desirable to provide a sustained heat source to the afflicted area for as long as possible, i.e., from about twenty minutes to about twelve hours, preferably from about four hours to about twelve hours, most preferably from about eight hours to about twelve hours. Disposable heat packs based on iron oxidation, such as those described in U.S. Pat. Nos. 4,366,804, 4,649,895, 5,046,479 and Re. 32,026, are known. However, such devices have proven not totally satisfactory because many of these devices are bulky, cannot maintain a consistent and controlled temperature, and have unsatisfactory physical dimensions, which hinder their effectiveness. Specifically, such devices cannot be easily incorporated into pads which can comfortably conform to various body contours, and hence, they deliver short duration, inconsistent, inconvenient and/or uncomfortable heat application directly to the body.

The present inventors have discovered disposable thermal body pads comprising one or more thermal packs having a unified structure, wherein each thermal pack has at least one continuous layer of a semirigid material which is sufficiently rigid in specific areas of the thermal pack, yet which softens in between such areas when heated during use, preferably comprising a coextruded film of polypropylene and EVA. The thermal pack or packs also comprise a plurality of individual heat cells, which typically comprise an exothermic composition, preferably comprising a specific iron oxidation chemistry and having specific physical dimensions and fill characteristics, spaced apart and fixedly attached across the thermal pack. Active heat cells, that is, heat cells having a temperature of from about 39° C. to about 60° C., preferably from about 40° C. to about 48° C., more preferably from about 41° C. to about 47° C., most preferably from about 42° C. to about 45° C., preferably soften narrow portions of the continuous layer or layers of semirigid, material which immediately surround the heat cells. All remaining portions of the continuous layer or layers which surround the softened portions remain more rigid. The narrow, softened portions act as hinges between each heat cell and the remaining, cooler, more rigid portions, bending preferentially more than either the heat cell or the more rigid portions. This results in thermal packs which possess sufficient rigidity to maintain structural support of the heat cells, to prevent unacceptable stretching of structures of the continuous layer or layers during processing or use, and to ensure child resistance, while still maintaining good overall drape characteristics when heated. The thermal pack or packs, when incorporated into the disposable thermal body pads of the present invention, provide uniform heat coverage by having excellent conformity with the user's body.

It is therefore an object of the present invention to provide disposable thermal body pads comprising one or more thermal packs having a unified structure of at least one continuous layer of semirigid material, which has different stiffness characteristics over a range of temperatures, and a plurality of individual heat cells, which provide a controlled and sustained temperature and which reach their operating temperature range relatively quickly. The heat cells are spaced apart and fixedly attached across the thermal pack.

It is a further object of the present invention to provide disposable thermal body pads having good overall drapability while maintaining sufficient rigidity to maintain structural support of the heat cells and prevent unacceptable stretching of the continuous layer or layers during processing or use.

It is a still further object on the present invention to provide disposable thermal body pads which adapt to a wide variety of body contours providing consistent, convenient and comfortable heat application while ensuring child resistance.

It is another object of the present invention is to provide disposable thermal body pads comprising a means for attaching the thermal body pad to a user's clothing so that the opposite side of the thermal body pad may be worn directly against the user's skin.

These objectives and additional objectives will become readily apparent from the detailed description which follows.

SUMMARY OF THE INVENTION

The disposable thermal body pads of the present invention comprise a substantially planar laminate structure having a first side, a second side, and one or more thermal packs comprising a unified structure having at least one continuous layer of coextruded material comprising a first side of polypropylene and a second side of a low melt temperature copolymer, which has different stiffness characteristics over a range of temperatures. Thermal packs further comprising a plurality of heat cells spaced apart which provide controlled and sustained temperature and which reach their operating temperature range quickly. The heat cells are preferably embedded between the first and the second sides and fixedly attached within each thermal pack. Each thermal pack provides good dependability while maintaining sufficient rigidity to maintain structural support of the heat cells and to prevent unacceptable stretching of the continuous layer or layers during processing or use, providing consistent, convenient and comfortable heat application. The laminate structure has means for providing oxygen permeability to each of the plurality of heat cells. The means for providing oxygen permeability is preferably located on the first side of the laminate structure. The disposable thermal body pad also comprises means for releasably attaching the thermal body pad to an inside portion of a user's clothing. The means for releasably attaching is located on the first side of the laminate structure so that the second side of the thermal body pad may be placed directly against a user's body.

The plurality of heat cells preferably has an oxygen activated, heat generating chemistry containing a mixture of powdered iron, powdered activated charcoal, vermiculite, water and salt.

The means for providing oxygen permeability may comprise an impermeable layer of the laminate structure having a pattern of apertures therethrough providing air communication with the heat generating chemistry. Such a pattern of apertures is located over each of the plurality of heat cells. The pattern of apertures is sized to control oxygen permeability and thereby control temperature generated in the heat cells.

The means for releasably attaching the thermal body pad may comprise pressure sensitive adhesive. The laminate structure has an upper edge and a lower edge, and the pressure sensitive adhesive may be placed in parallel stripes extending continuously from the upper edge to the lower edge between the plurality of heat cells. Alternatively, the pressure sensitive adhesive is applied in narrow intermittent strands partially covering the first side such that the means for providing oxygen permeability on the first side maintains an acceptable level of oxygen permeability.

The disposable thermal body pad may further comprise an air impermeable envelope surrounding the disposable thermal body pad. The thermal body pad preferably remains sealed inside the air impermeable envelope until a user is ready to apply the thermal body pad to the user's clothing. Opening the air impermeable envelope enables oxygen from ambient air to activate the plurality of heat cells to generate controlled and sustained heating.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
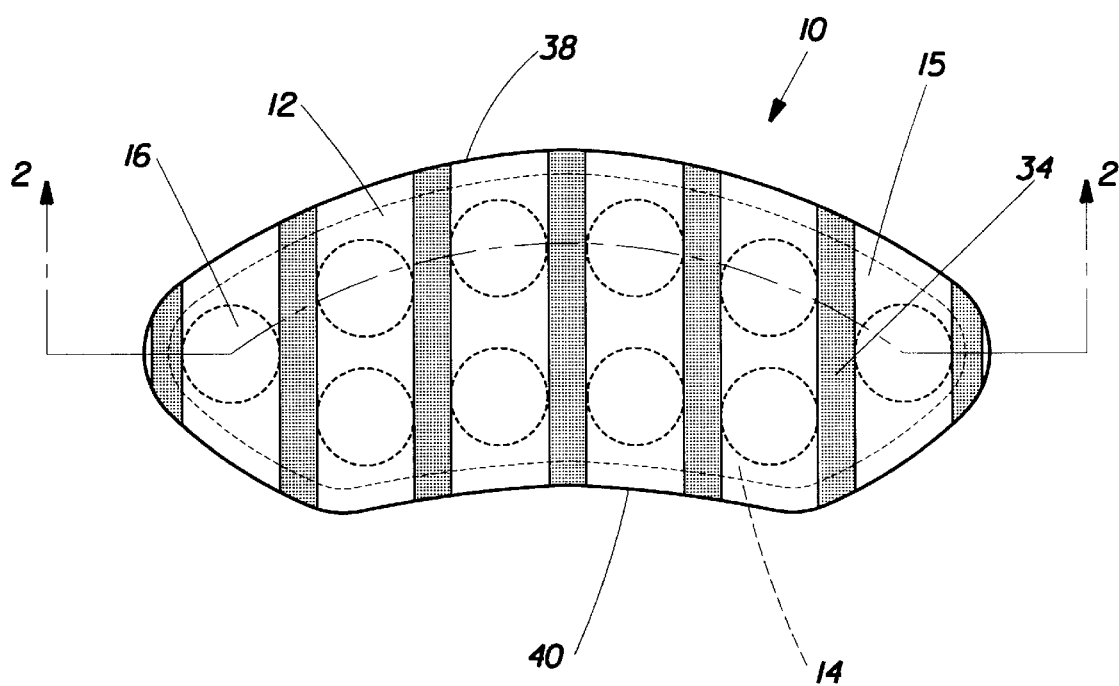
FIG. 1 is a plan view of a preferred embodiment of the disposable thermal body pad of the present invention, disclosing a pattern of heat cells and attachment adhesive stripes between the cells.

The disposable thermal body pads of the present invention comprise one or more thermal packs having at least one continuous layer of a material, which exhibits specific thermophysical properties. The material is semirigid when at room temperature, i.e., about 25° C., or below, but softens and becomes substantially less rigid when heated to about 45° C. Therefore, when heat cells, which are fixedly attached to the structure of the thermal packs, are active, that is at a heat cell temperature of from about 39° C. to about 60° C., preferably from about 40° C. to about 48° C., more preferably from about 42° C. to about 47° C., and most preferably from about 44° C. to about 45° C., the narrow portion of the continuous layer or layers of material immediately surrounding each heat cell softens and acts as a hinge between the heat cell and the remaining, cooler, more rigid portion of the continuous layer or layers, bending preferentially more than either the heat cell or the more rigid portion. This results in thermal packs which possess sufficient rigidity to maintain structural support of the heat cells and prevent unacceptable stretching of structures of the continuous layer or layers during processing or use, while still maintaining good overall drape characteristics when heated. The disposable thermal body pads of the present invention provide consistent, convenient, and comfortable heat application, and an excellent conformity with user's body, while retaining sufficient rigidity to ensure child resistance.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Semirigid material", as used herein, means a material which is rigid to some degree or in some parts and exhibits a toughness to maintain structural support of the heat cells in an unsupported format, and/or prevent unacceptable stretching of structures of the material during processing or use, while still maintaining good overall drape characteristics when heated, and/or retaining sufficient rigidity to ensure child resistance.

"Two dimensional drape", as used herein, means drape which occurs across a continuous layer or layers, across a thermal pack, or across a select region of a layer or layers, or thermal pack, exclusively along one axis, i.e., one fold line forms, at the expense of other axes in response to gravitational pull or other modest forces.

"Three dimensional drape", as used herein, means drape which simultaneously occurs across a continuous layer or layers, across a thermal pack, or across a select region of a layer or layers, or thermal pack, among two or more axes in response to gravitational pull or other modest forces.

It is understood that the disposable thermal body pads of the present invention may comprise one or more thermal packs. However, for clarity a disposable thermal body pad comprising a single thermal pack will be described herein.

Figure 2:
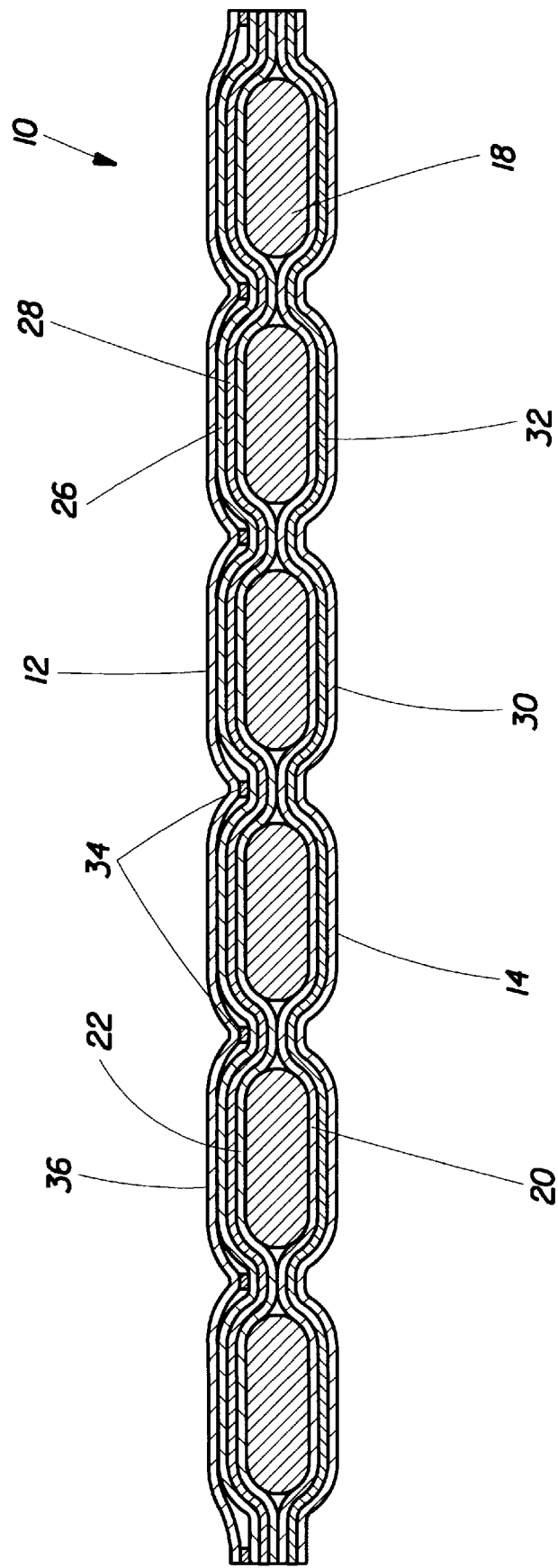
FIG. 2 is sectioned side elevation of FIG. 1.

Referring now to the drawings, and more particularly to FIGS. 1 and 2, there is shown a preferred embodiment of the present invention, which provides a thermal body pad having a substantially planar laminate structure. The laminate structure has a common attachment and oxygen permeable side, and is generally indicated as 10. Thermal body pad 10 comprises a first side 12, which is positioned away from the body during wear, and a second side 14, which is postioned against the body, and one or more thermal packs 15.

Each thermal pack 15 comprises a plurality of individual heat cells 16, preferably embedded within the laminate structure of the thermal pack 15. These heat cells 16 are spaced apart from each other and each heat cell 16 functions independently of the rest of the heat cells 16. Each heat cell 16 contains a densely packed, particulate exothermic composition 18 which substantially fills the available cell volume within the cell reducing any excess void volume thereby minimizing the ability of the particulate matter to shift within the cell. Alternatively, the exothermic composition 18 may be compressed into a hard tablet before being placed in each cell. Because the heat generating material is densely packed or compressed into a tablet, the heat cells 16 are not readily flexible. Therefore, the spacing apart of the cells and the materials selected for cell forming base layer 20 and cell covering layer 22 between the heat cells 16 allows each thermal pack 15 to easily conform to the user's body.

Alternatively, each thermal pack 15 may comprise a single continuous base layer 20, wherein individual heat cells 16 are fixedly attached and spaced apart across the base layer 20.

Cell forming base layer 20 and cell covering layer 22 may be made of any number of thermoplastic materials which are semirigid at a temperature of about 25° C. and which soften, i.e., become substantially less rigid, at a temperature of about 45° C. Different materials may be capable of satisfying the specified requirement provided that the thickness is adjusted accordingly. Such materials include, but are not limited to, films of polyethylene, polypropylene, polyester, styrene block copolymers, film coated nonwovens, laminates, permeable membranes, and mixtures thereof. These materials may be used alone or coextruded with a low melt temperature polymer including, but not limited to, ethylene vinyl acetate copolymer, low density polyethylene, and mixtures thereof. Such materials are also capable of containing exothermic composition 18 and limiting oxygen flow into the heat cell 16, of providing sufficient rigidity to prevent thermal pad 10 from folding or bunching during use, of preventing unacceptable stretching of structures of the continuous layer during processing or use, and of ensuring child resistance.

Cell forming base layer 20 and cell covering layer 22 preferably comprise a coextruded film, having a first side of polypropylene and a second side of EVA, and having a combined thickness of from about 20 $\mu$m to about 30 $\mu$m, preferably about 25 $\mu$m. The polypropylene comprises from about 10% to about 90%, preferably from about 40% to about 60%, of the thickness of cell forming base layer 20 and cell covering layer 22. When coextruded films of the type just described are used for cell forming base layer 20 and cell covering layer 22, the EVA sides are preferably orientied toward each other to facilitate thermal bonding of cell covering layer 22 to cell forming base layer 20. A particularly suitable material is available as P18-3161 from Clopay Plastics Products, Cincinnati, Ohio, or Terre Haute, Ind. The P18-3161 which is suitable for cell covering layer 22 has been subjected to a post process aperturing with hot needles to render it permeable to oxygen.

When coextruded films of the type just described are used for cell forming layer 20 and cell covering 22, the EVA sides are preferably oriented toward each other to facilitate thermal bonding of cell covering 22 to cell forming layer 20.

Oxygen permeability in cell covering layer 22 is preferably a plurality of apertures in cell covering layer 22, which are made by piercing cell covering layer 22 with hot needles. The size of the apertures is preferably about 0.127 mm diameter, and there are preferably 25 to 40 apertures per heat generating cell. Another preferred method of making apertures is to pierce cell covering layer 22 with cold needles. Alternatively, apertures may be produced by a vacuum forming or a high pressure water jet forming process. Yet another method is making cell covering layer 22 from a microporous membrane or a semipermeable membrane. Such membrane may be combined with a highly porous carrier material to facilitate processing. The oxygen permeability required ranges from about 0.01 cc $O_2$ per minute per 5 square cm to about 15 cc $O_2$ per minute per 5 square cm at 21° C. and 1 atm.

Exothermic composition 18 may comprise any composition capable of providing heat. However, exothermic composition 18 preferably comprises a particulate mix of chemical compounds that undergo an oxidation reaction during use. Exothermic composition 18 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type react when exposed to oxygen, providing heat for several hours.

The compaction articles of the present invention are typically compressed to a density of greater than about 1 g/cm$^3$, preferably from about 1 g/cm$^3$ to about 3 g/cm$^3$, more preferably from about 1.5 g/cm$^3$ to about 3 g/cm$^3$, and most preferably from about 2 g/cm$^3$ to about 3 g/cm$^3$.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Typically, agglomeration aids comprise from about 0% to about 90%, preferably from about 0.5% to about 8%, more preferably from about 0.6% to about 6%, most preferably from about 0.7% to about 3% by weight, of the agglomerated pre-compaction compositions of the present invention. The amount of dry binder added to the compositions of the present invention depend on the degree of hardness desired. Dry binders typically comprise from about 0% to about 35%, preferably from about 4% to about 30%, more preferably from about 7% to about 20%, most preferably from about 9% to about 15% by weight, of the agglomerated pre-compaction compositions of the present invention.

The heat cells 16 of each thermal pack 15 can have any geometric shape, e.g., disk, triangle, pyramid, cone, sphere, square, cube, rectangle, rectangular parallelepiped, cylinder, ellipsoid and the like. The preferred shape of the heat cells 16 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 16 have a height of from about 0.08 cm to about 1 cm, preferably from about 0.15 cm to about 0.9 cm, more preferably greater than from about 0.2 cm to about 0.8 cm, and most preferably about 0.4 cm.

The ratio of fill volume to cell volume of the heat cells 16 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

The plurality of heat cells 16 are spaced apart from each other, and each cell is functions independently from the rest. Because the chemistry is densely packed in each cell, spacing apart heat cells 16 enables the thermal body pad to conform to the contours of the body more readily than a single large cell. The chemistry may even be compressed into a tablet in each cell. The cells therefore do not readily flex, but the material between the cells does flex, thereby providing for body conformity.

Preferably, each heat cell 16 has a similar volume of chemistry and has a similar oxygen permeablity means 24. Alternatively, chemistry volumes, shapes, and oxygen permeability means can be different from cell to cell as long as the resulting cell temperatures generated are similar.

On either side of heat cells 16 of thermal pack 15 are additional layers of material. On first side 12 is a first outer fabric 26 attached to cell covering layer 22 by a first adhesive layer 28. First outer fabric 26 and first adhesive layer 28 are preferrably more permeable to air than is cell covering layer 22. Furthermore, first outer fabric 26 and first adhesive layer 28 preferably do not appreciably alter the oxygen permeability of cell covering layer 22. Therefore, cell covering layer 22 alone controls the flow rate of oxygen into each heat generating cell 16.

On second side 14 of thermal body pad 10 is a second outer fabric 30, which is attached to cell forming layer 20 by a second adhesive layer 32. Preferably, first outer fabric 26 and second outer fabric 30 are made of similar materials, and first adhesive layer 28 and second adhesive layer 32 are made of the same materials.

First side 12 of thermal body pad 10 has an attachment means 34 for releasably attaching thermal body pad 10 to clothing. Attachment means 34 may be an adhesive. If an adhesive, then attachment means 34 may have a release paper 36 attached to the adhesive in order to protect adhesive 34 from prematurely sticking to a target other than the intended user's clothing. Attachment means 34 preferably has a stronger bond to first outer fabric 26 than to either release paper 36 or to any target surface.

Alternatively, attachment means 34 may be an adhesive coated film attached to first outer fabric 26. If the adhesive coated film has standoffs to prevent adhesion until the target surface and the film are pressed together to expose the adhesive, then release paper 36 may be eliminated. Attachment means 34 may also comprise mechanical fasteners attached to first outer fabric 26, which provide sufficient engagement with different varieties of clothing to enable fixed positioning to be achieved. If mechanical fasteners are used, release paper 36 may also be eliminated.

Thermal body pad 10 has an upper edge 38 and a lower edge 40 opposite the pad from upper edge 38. These edges are so designated because of the orientation of the pad when it is used as a menstrual pain heating pad and placed inside a woman's panties to rest against her abdomen. Attachment means 34 are used to attach thermal body pad 10 to inner surface of clothing after release paper 36 has been removed.

Attachment means 34, for releasably attaching thermal body pad 10 to clothing, may be any number of suitable adhesives and application patterns. A preferred adhesive is Dispomelt™ 34-5598 pressure sensitive hot melt adhesive available from National Starch and Chemical Company of Bridgewater, N.J. This adhesive may be applied to first outer fabric 26 by slot die coating or printing. In either case it is desirable that the adhesive penetrate into first outer fabric 26 so that the adhesive preferentially sticks to first outer fabric 26 upon removal of thermal body pad 10 from the user's clothing after use. The pattern of adhesive produced by this method may be straight parallel stripes extending from upper edge 38 to the lower edge 40 of thermal body pad 10, and located between heat cells 16, as depicted in FIG. 1. The relatively heavy adhesive stripes are oxygen impermeable. By positioning the stripes of adhesive between heat cells 16, oxygen permeability of cell covering layer 22 remains unhindered in its ability to pass oxygen to heat cells 16. Release paper 36 is preferably a silicone treated paper, such as BL 25 MGA SILOX C3R/0 release paper from Akrosil, Menasha, Wis.

In a particularly preferred embodiment of the present invention, first outer fabric 26 is preferably a soft flexible material. Materials suitable as first outer fabric 26 include, but are not limited to, formed films; fabrics including wovens, knits, and nonwovens, which are carded, spunbonded, air laid, thermally bonded, wet laid, meltblown, and/or through-air bonded. The material compostion of first outer fabric 26 may be cotton, polyester, polyethylene, polypropylene, nylon, etc. A particularly suitable material for first outer fabric is 32 grams per square meter (gsm), hydrophobic, polypropylene, carded thermal bonded fabric available as grade #9327786 from Veratec, Walpole, Mass.

Preferably, second outer fabric 30 is a soft, flexible, non-irritating-to-the-skin material. Materials suitable as second outer fabric 30 include but are not limited to: formed films; fabrics including wovens, knits, and nonwovens, which are carded, spunbonded, air laid, thermally bonded, wet laid, meltblown, and/or through-air bonded. The material of second outer fabric 30 may be cotton, polyester, polyethylene, polypropylene, nylon, etc. A particularly suitable material for second outer fabric 30 is 63 gsm polypropylene carded thermally bonded fabric available as grade #9354790 from Veratec, Walpole, Mass.

Adhesive layer 28 is applied in such a manner that it does not interfer with oxygen permeability to heat cells 16. A suitable material and application method that has been succesfully used for adhesive layers 28 and 32 are 70-4589 pressure sensitive hot melt adhesive available from National Starch and Chemical Co., Bridgewater, N.J., which is applied with spiral glue application system available from Nordson, Waycross, Ga.

Prior to use, thermal body pad 10 is typically enclosed within an oxygen impermeable package. Thermal body pad 10 is preferably folded in half with second side 14 internal to the fold and external side 12 exposed to the inside of the package. Thermal body pad 10 is removed from the oxygen impermeable package allowing oxygen to react with chemistry 18. This chemical oxidation system is compact and portable. Once the chemical reaction is completed, the thermal body pad is no longer capable of generating heat and it is intended to be appropriately discarded in the solid waste system.

By placing the attachment means on the same side as the oxygen permeable layer, the thermal body pad of the present invention may be worn inside a user's clothing and directly in contact with the user's body. Such direct contact by heat cells in the thermal body pad provides a known thermal resistance between heat generating chemistry and body surface. Thus, the chemistry can be designed to oxidize at a particular rate to produce a specified temperature.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal body pad comprising:
   a) at least one piece of flexible material having a first side, a second side, an upper edge, a lower edge, and one or more thermal packs fixed within or to said at least one piece of flexible material, which comprise a unified structure of at least one continuous layer, which consists essentially of a coextruded material having a first side of polypropylene and a second side of a low melt temperature copolymer wherein said continuous layer is semirigid at a temperature of about 25° C. and substantially less rigid at a temperature of about 45° C., and a plurality of individual heat cells spaced apart and fixed within or to said unified structure of said thermal pack; and
   b) a means for releasably attaching said thermal body pad to an inside portion of user's clothing, said means for releasably attaching said thermal body pad being located on said first side of said flexible material so that said second side of said flexible material may be placed directly against a user's body.

2. The disposable thermal body pad of claim 1 wherein said means for releasably attaching said thermal pad comprises pressure sensitive adhesive.

3. The disposable thermal body pad of claim 2 wherein said unified structure has an upper edge and a lower edge, and wherein said pressure sensitive adhesive is placed in parallel stripes extending continuously from said upper edge to said lower edge between said plurality of heat cells.

4. A disposable thermal body pad according to claim 1 wherein said continuous layer comprises a coextruded film having a first side of polypropylene and a second side of ethylene vinyl acetate copolymer, wherein said polypropylene comprises from about 10% to about 90% of the total thickness of said film.

5. A disposable thermal body pad according to claim 4 wherein said continuous layer comprises a coextruded film having a first side of polypropylene and a second side of ethylene vinyl acetate copolymer, wherein said polypropylene comprises from about 40% to about 60% of the total thickness of said film.

6. A disposable thermal body pad according to claim 5 wherein said continuous layer has a thickness of from about 20 μm to about 30 μm.

7. A disposable thermal body pad according to claim 1 wherein said heat cells comprise an exothermic composition which comprises:
   a.) from about 30% to about 80% iron powder;
   b.) from about 3% to about 25% activated carbon, non-activated carbon, and mixtures thereof;
   c.) from about 0.5% to about 10% metal salt; and
   d.) from about 1% to about 40% water.

8. A disposable thermal body pad according to claim 7 wherein said heat cells comprise from about 0.1% to about 30% of additional water-holding material.

9. A disposable thermal body pad according to claim 7 wherein said heat cells comprise a shape selected from the group consisting of a disk, triangle, pyramid, cone, sphere, square, cube, rectangle, rectangular parallelepiped, cylinder, and ellipsoid.

10. A disposable thermal body pad according to claim 9 wherein said heat cells comprise the shape of a disk having a diameter of from about 0.2 cm to about 10 cm and a height of greater than from about 0.2 cm to about 1.0 cm.

11. A disposable thermal body pad according to claim 1 wherein said heat cells comprise an exothermic composition which comprises:
   a.) from about 30% to about 80% of iron powder;
   b.) from about 3% to about 20% of carbonaceous material selected from the group consisting of activated carbon, non-activated carbon, and mixtures thereof;
   c.) from about 0% to about 9% of an agglomeration aid selected from the group consisting of corn syrup, maltitol syrup, crystallizing sorbitol syrup, amorphous sorbitol syrup, and mixtures thereof; and
   d.) from about 0% to about 35% of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;

wherein from about 0.5% to about 10% of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof.

12. A disposable thermal body pad according to claim 11 wherein said heat cells further comprise from about 0.5% to about 10% of additional water-holding materials selected from the group consisting of acrylic acid salt starch co-polymer, isobutylene maleic anhydride co-polymer, vermiculite, carboxymethylcellulose, and mixtures thereof.

13. A disposable thermal body pad according to claim 11 wherein said dry binder comprises from about 4% to about 30% of microcrystalline cellulose.

14. A disposable thermal body pad according to claim 11 wherein said metal salt comprises sodium chloride.

15. A disposable thermal body pad according to claim 11 wherein said exothermic composition further comprises from about 1% to about 40% by weight, of water.

16. A disposable thermal body pad according to claim 11 wherein said direct compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid.

17. A disposable thermal body pad according to claim 16 wherein said tablets and slugs comprise a disk shaped geometry having a diameter of from about 0.2 cm to about 10 cm and a height of from about 0.08 cm to about 1.0 cm.

18. A disposable thermal body pad according to claim 17 wherein said tablets comprise a geometric shape selected from the group consisting of a disk shape wherein a hole passes perpendicular to and through the middle of the top and bottom surfaces and a disk shape wherein the top and bottom surfaces are concaved forming a reservoir conducive to holding a liquid.

19. A disposable thermal body pad according to claim 18 wherein said tablets comprise a disk shape wherein a hole passes perpendicular to and through the middle of the top and bottom surfaces.

20. A disposable thermal body pad according to claim 16 wherein said direct compaction articles comprise a density of greater than about 1 g/cm$^3$.

21. A disposable thermal body pad according to claim 20 wherein said direct compaction articles comprise a density of from about 1.5 g/cm$^3$ to about 3.0 g/cm$^3$.

* * * * *